United States Patent [19]

Michaels

[11] Patent Number: 5,099,833
[45] Date of Patent: Mar. 31, 1992

[54] HIGH EFFICIENCY NEBULIZER HAVING A FLEXIBLE RESERVOIR

[75] Inventor: Thomas L. Michaels, Valencia, Calif.
[73] Assignee: Baxter International Inc., Deerfield, Ill.
[21] Appl. No.: 656,323
[22] Filed: Feb. 19, 1991
[51] Int. Cl.⁵ ............................................. A61M 11/00
[52] U.S. Cl. ............................ 128/200.14; 128/200.16; 128/203.12
[58] Field of Search .................. 128/200.14, 200.16, 128/200.23, 203.12, 203.28, 205.13, 205.14, 205.17

[56] References Cited

U.S. PATENT DOCUMENTS

| | | | |
|---|---|---|---|
| 2,119,446 | 5/1938 | Sholes | 128/203.28 |
| 2,185,067 | 12/1939 | Sholes | 128/203.28 |
| 2,208,633 | 7/1940 | Heidbrink | 128/203.28 |
| 3,769,973 | 11/1973 | Esbenshade, Jr. | 128/200.14 |
| 4,174,712 | 11/1979 | Moren et al. | 128/200.14 |
| 4,396,015 | 8/1983 | Johnson | 128/200.14 |
| 4,484,577 | 11/1984 | Sackner et al. | 128/203.28 |
| 4,534,343 | 8/1985 | Nowacki et al. | 128/200.23 |
| 4,676,239 | 6/1987 | Humphrey | 128/205.17 |
| 4,823,784 | 4/1989 | Bordoni et al. | 128/200.16 |
| 4,938,210 | 3/1990 | Shene | 128/203.12 |

OTHER PUBLICATIONS

Photograph dated Jan. 10-12, 1991—"Ultrasonic Nebulizer".
Paul Ritzau Pari-Werk GmbH Brochure.

Primary Examiner—Edgar S. Burr
Assistant Examiner—Aaron J. Lewis
Attorney, Agent, or Firm—Kay H. Pierce; Paul C. Flattery

[57] ABSTRACT

A medication aerosol delivery system is described. The system is unique in that it includes a flexible reservoir for receiving medicated aerosol from a nebulizer when a patient is not inhaling. The aerosol in the reservoir can be later inhaled during the next patient inhalation. The threshold filling pressure (the pressure required for aerosol to enter the reservoir) is less than a threshold opening pressure of a one-way valve that is located between the reservoir and the patient. The medication system described herein has an increased efficiency over other medication systems without a reservoir because it allows medicated aerosol to be collected in a reservoir between patient inhalations.

5 Claims, 4 Drawing Sheets

HIGH EFFICIENCY NEBULIZER HAVING A FLEXIBLE RESERVOIR

BACKGROUND OF THE INVENTION

This invention relates generally to nebulizers for use in respiratory therapy and more specifically to nebulizer systems which include a flexible reservoir for retaining nebulized aerosols between patient inhalations.

In the field of respiratory therapy, it is sometimes desired to provide a patient with a medication that has been disbursed into very small particles using a nebulizer. In such therapies, a patient typically breaths the nebulized air through a mouthpiece and exhales through the same mouthpiece. The mouthpiece is generally connected to a manifold which includes both an inlet port and an outlet port. A nebulizer is typically in communication with the inlet port. Medicated aerosol thus enters the patient from the inlet port of the manifold. In most applications, the inlet port and the outlet port of the manifold are in fluid communication with one another. This allows any excess pressurized air coming from the nebulizer to be exhausted through the outlet port of the manifold when a patient is not inhaling. One problem with such a system is that is inefficient in that it allows medicated aerosol to be lost.

One method for overcoming this problem has been to include a rigid chamber for receiving excess medicated aerosol from the nebulizer when the patient is not inhaling. Typically, this rigid chamber may also include a one-way valve which serves to prevent aerosol from flowing out into the room. However, if the rate in which a patient is inhaling is greater than the flow rate the nebulizer, the one-way valve allows room air to enter the aerosol delivery system to make up for the deficiency in flow rate from the nebulizer. Accordingly, air flowing through this valve is commonly called "make-up room air". Since make-up room air typically flows through the rigid chamber during patient inhalations, the chamber remains essentially full at all times. Accordingly, in between patient inhalations, it has been found that only a small percentage of medicated aerosol actually enters the rigid chamber rather than exiting the system by flowing through the manifold to the outlet port.

One of the problems with respiratory therapy systems that include a rigid chamber as described above is that is can be undesirably expensive to provide certain medications to a patient. For instance, pentamidine isethionate is a relatively expensive drug that is currently being administered as a small-particle aerosol to patients having Pneumosystis carinii pneumonia. Currently, the cost of administering this medication to a patient may be as much as $200 per treatment. If a system can be developed which is 50 percent more efficient in administering the medication to a patient, the cost of the medication can be reduced by 50 percent.

Another problem with administering an aerosol in which large portions of the aerosol are not inhaled by a patient is that is can be difficult to determine how much medication a patient has actually received during an individual treatment. If it is possible to efficiently collect the aerosol between inhalations and use that aerosol (rather than make-up room air) during subsequent inhalations, the amount of medication actually received by a patient may be more accurately estimated.

Yet another problem with systems in which an aerosol is inefficiently administered to a patient is that the treatment time is directly related to the efficiency of the aerosol delivery system. This problem is particularly acute when it is necessary to deliver the medication as a small particle aerosol. For purposes of this application, small particles are considered to be in the range of 0.3 to 2.0 microns. Currently, only a small amount of drug is available during each inhalation because it is limited by the amount that can be nebulized during that inhalation time. By providing a system which can efficiently collect and store medicated aerosol between inhalations and add that aerosol to aerosol being generated during a patient's inhalation, it is possible to increase the mass of drug inhaled during each inhalation.

Therefore, a need existed to develop a system for efficiently and effectively collecting small particle aerosols between patient inhalations and delivering such collected aerosol to patients during the next inhalation.

A need also existed to develop an increased efficiency aerosol delivery system which capable of being manufactured at a relatively low cost.

A need also existed to develop an increased efficiency aerosol delivery system which could be easily tolerated by a patient during use.

These and other needs have each been met by the device described below.

SUMMARY OF THE INVENTION

A filtered medication aerosol delivery system is described for delivering a small particle aerosol to a patient. The system includes a manifold that has an inlet leg, an outlet leg, and a patient breathing leg. Each of the legs of the manifold are in fluid communication with one another at a common juncture. The inlet leg also includes each of the components discussed below in fluid communication with one another. The inlet leg includes a medication nebulizer for introducing a medicated aerosol into the inlet leg of the manifold. Also included in the inlet leg is a flexible reservoir for receiving medicated aerosol between patient inhalations. The inlet leg also includes a first one-way valve located between the common juncture and both of the nebulizer and the flexible reservoir to allow air to flow in one direction only from said inlet leg to said patient breathing leg and said outlet leg. The first one-way valve ahs a threshold opening pressure. The flexible reservoir has a threshold filling pressure and a threshold collapsing pressure. The threshold filling pressure of the flexible reservoir is less than the threshold opening pressure of the one-way valve. The relationship between the threshold filling pressure and the threshold opening pressure prevents medicated aerosol from escaping into the common juncture between patient inhalations. Since the medicated aerosol cannot pass through the first one-way valve, it is collected in the flexible reservoir until the next patient inhalation. When the next patient inhalation begins, the pressure differential across the first one-way valve causes the valve to open and allows nebulized medication from the nebulizer and nebulized medication collected in the flexible reservoir to enter into the patient breathing leg to be inhaled by the patient.

DETAILED DESCRIPTION OF THE PREFERRED EMBODIMENT

Figure 1:
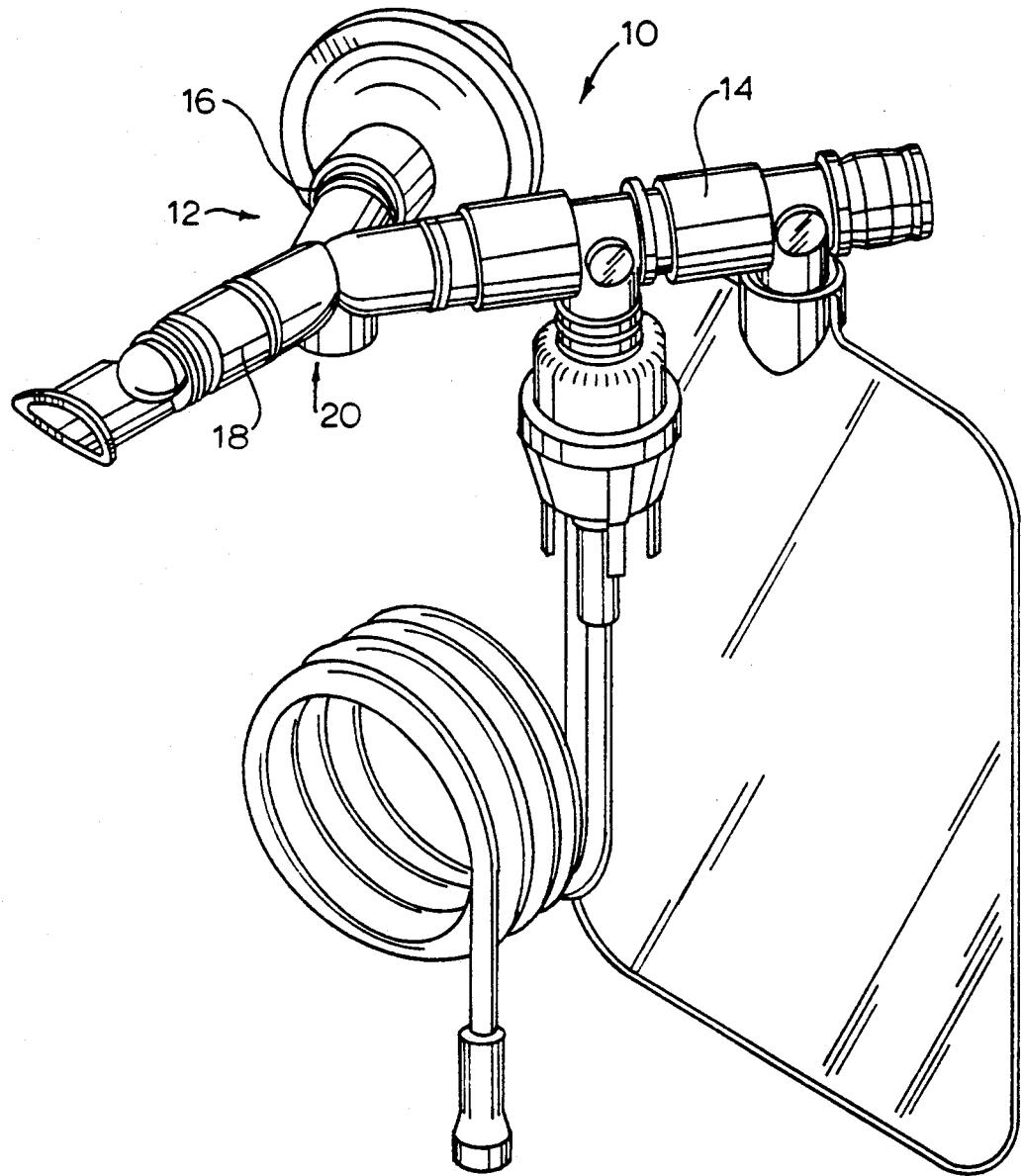
FIG. 1 is a perspective view of one embodiment of the invention.

Refer now to FIG. 1 which is a perspective view of one embodiment of the subject invention. As can be seen in the figure, a filtered medication aerosol delivery system 10 is used to deliver a small particle aerosol to a patient. The system includes a manifold 12 that includes an inlet leg 14, an outlet leg 16 and a patient breathing leg 18. Each of the legs are in communication with one another through a common juncture 20. The inlet leg will now be described in greater detail.

Figure 3:
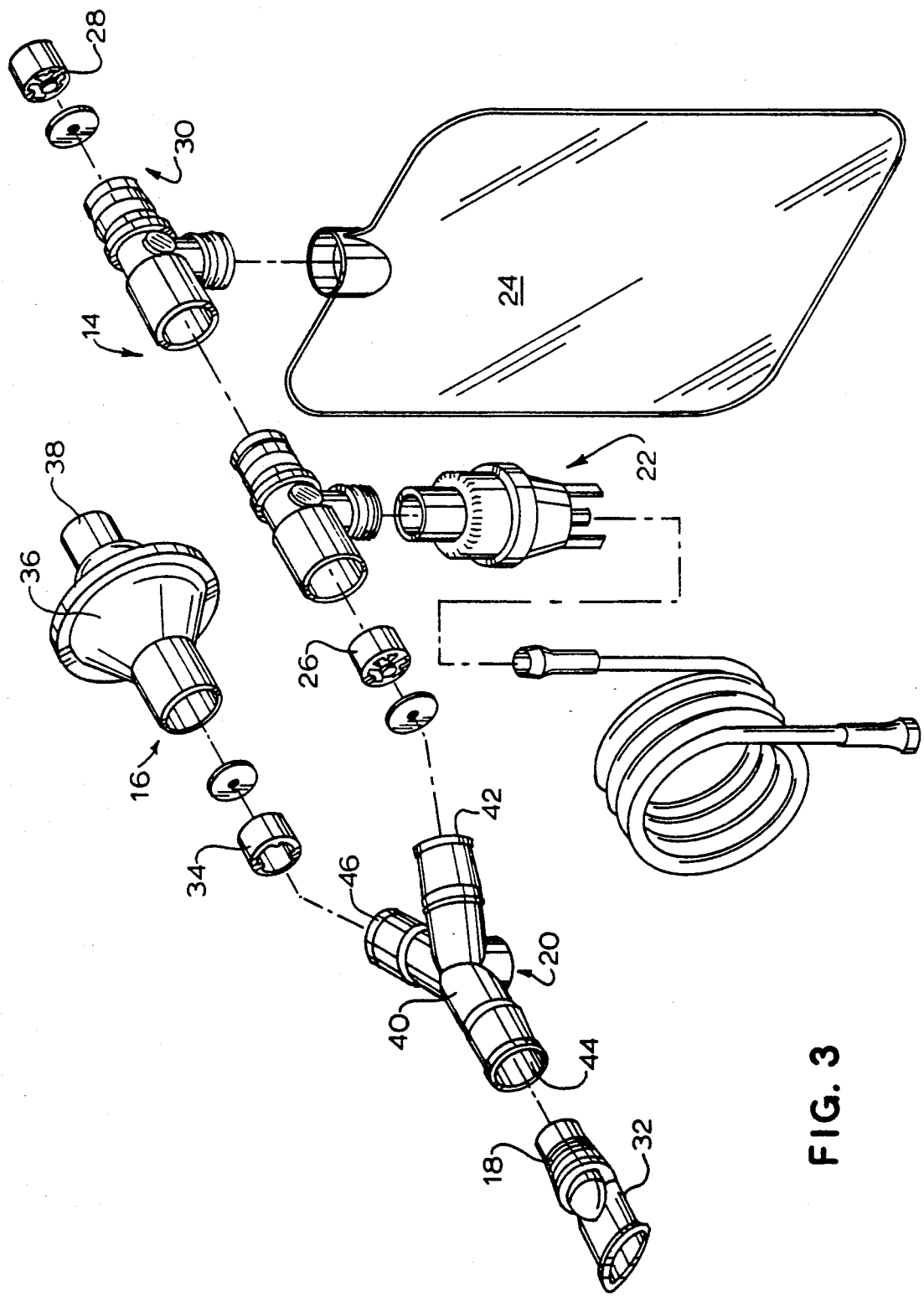
FIG. 3 is an exploded view of the embodiment of the invention illustrated in FIG. 1.

Refer now to FIG. 3. In one embodiment of the invention, the inlet leg 14 further includes the following elements in fluid communication with one another. The inlet leg 14 includes a medication nebulizer 22 for introducing a medicated aerosol into the inlet leg 14. The inlet leg 14 also includes a flexible reservoir 24 to receive medicated aerosol from the patient between patient inhalations. Finally, the inlet leg also includes a one-way valve 26 located between the common juncture 20 and both of the nebulizer 22 and the flexible reservoir 24. As discussed above, a purpose of the one-way valve is to prevent medicated aerosol from entering the common juncture 20 between patient inhalations. Instead, the medicated aerosol is allowed to enter the flexible reservoir 24.

A key to the invention is the relationship between the threshold opening pressure of valve 26 and the threshold filling pressure of reservoir 24. The threshold opening pressure (the pressure required to cause the one-way valve 26 to open) must be greater than the threshold filling pressure (the pressure required to cause the flexible reservoir 24 to separate or expand to receive medicated aerosol). By choosing a relatively flexible material to form the reservoir 24 and selecting a one-way valve based on its threshold opening pressure characteristics, it is possible to ensure that medicated aerosol generated by nebulizer 22 between patient inhalations does not escape through one-way valve 26 but is allowed to collect in reservoir 24.

In the preferred embodiment, as illustrated in FIG. 3, the nebulizer 22 is located between the one-way valve 26 and the reservoir 24. In one embodiment of the invention, another one-way valve 28 may be included in the inlet leg 14. The purpose of this valve is to allow room air to enter into the inlet leg 14 when the rate of patient inhalation exceeds the rate of flow available from the nebulizer 22 and the reservoir 24. This make-up room air has been previously discussed in the background of the invention. Although the valve 28 is illustrated at the distal end 30 of the inlet leg in FIG. 3, it should be noted that this valve 28 may be located anywhere along the inlet leg 14 as long as a separate outlet to room air is provided.

The patient breathing leg 18 includes a mouthpiece 32 through which a patient may inhale and exhale.

The outlet leg 16 includes a one-way valve 34 and a filter 36 in fluid communication with one another. Although a filter is illustrated in the preferred embodiment of the invention, in other embodiments of the invention, a filter may not be required. The purpose of the filter 36 is to filter medicated aerosol in instances in which the medication may be harmful to medical personnel or others present in the patient's room. the filter may also be used to filter contaiminants such as bacteria or other contagious organisms before a patient's exhalation is allowed to be emitted to room air. Although the filter 36 is illustrated at the distal end 38 of the outlet leg 16 in the embodiment illustrated in FIG. 3, in other embodiments, the relationship of the one-way valve and the filter may be exchanged.

The inlet leg 14, outlet leg 16, and patient breathing leg 18, are all in fluid communication with one another through a common juncture 20. In the preferred embodiment of the invention, as illustrated in FIG. 3, the common juncture 20 is a "Y" connection 40. The Y connection includes a first leg 42, a second leg 44, and a third leg 46. In the preferred embodiment of the invention, the first leg 42 of the common juncture is in fluid communication with one-way valve 26 of inlet leg 14. The second leg 44 of the common juncture is in fluid communication with the patient breathing leg 18. Finally, the third leg 46 is in fluid communication with one-way valve 34 of the outlet leg 16. Obviously, the relationship of the three legs of the Y connector may be interchanged. Also, in other embodiments, it may be desirable to use a "T" connector or another connection having a different configuration. The objective in using a Y connector is to allow the inlet and outlet legs 14, 16 to be displaced away from the patient's face to enhance patient comfort while using the delivery system 10.

Although a variety of configurations may be used, it is desirable to design a system in which the flexible reservoir 24 and the nebulizer 22 are in close proximity to the patient to prevent large amounts of volume to exist between the source of medicated aerosol and the patient. This enhances the efficiency of the system and reduces "rain out" of nebulized particles.

Figure 2:
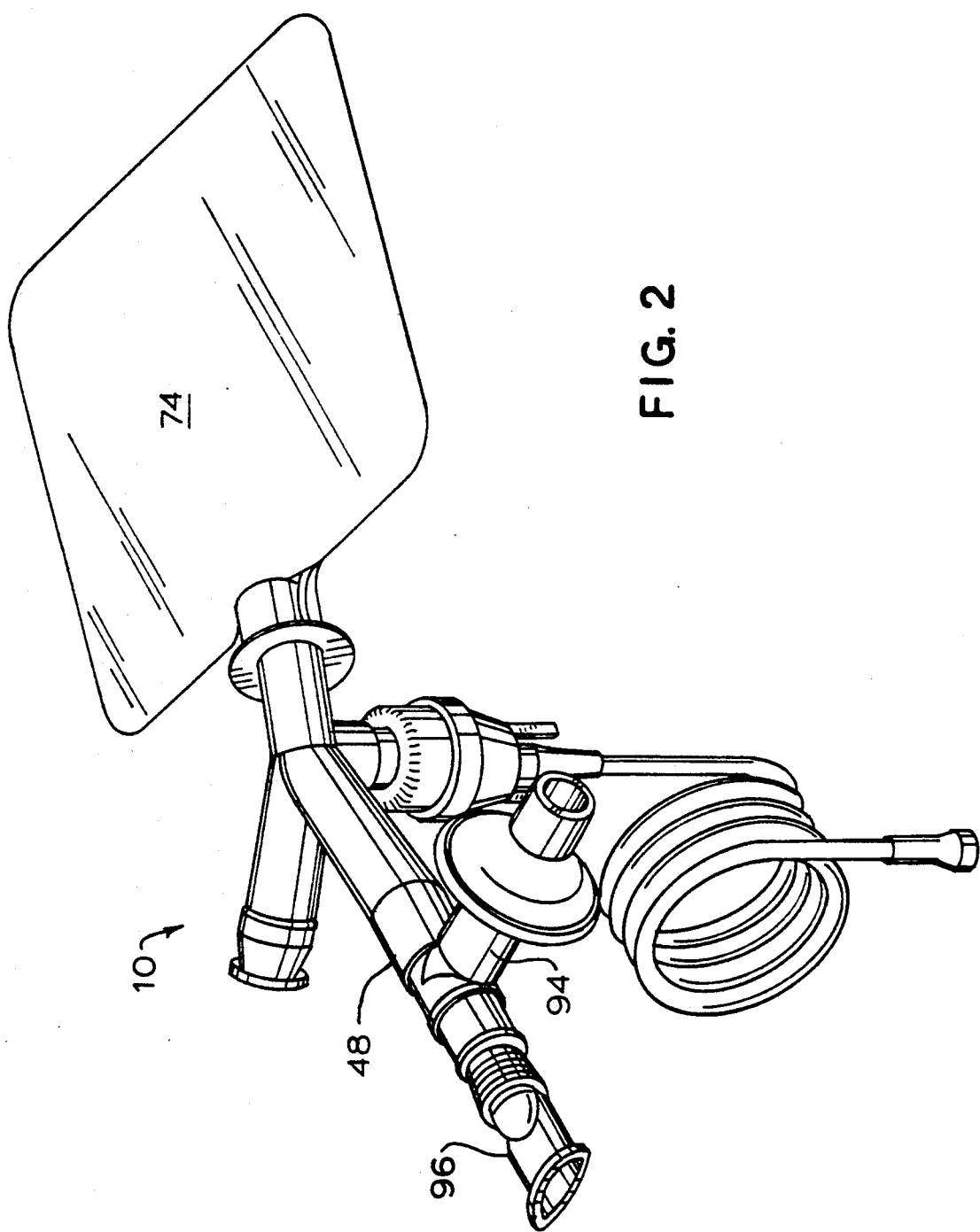
FIG. 2 is a perspective view of another embodiment of the invention.
Figure 4:
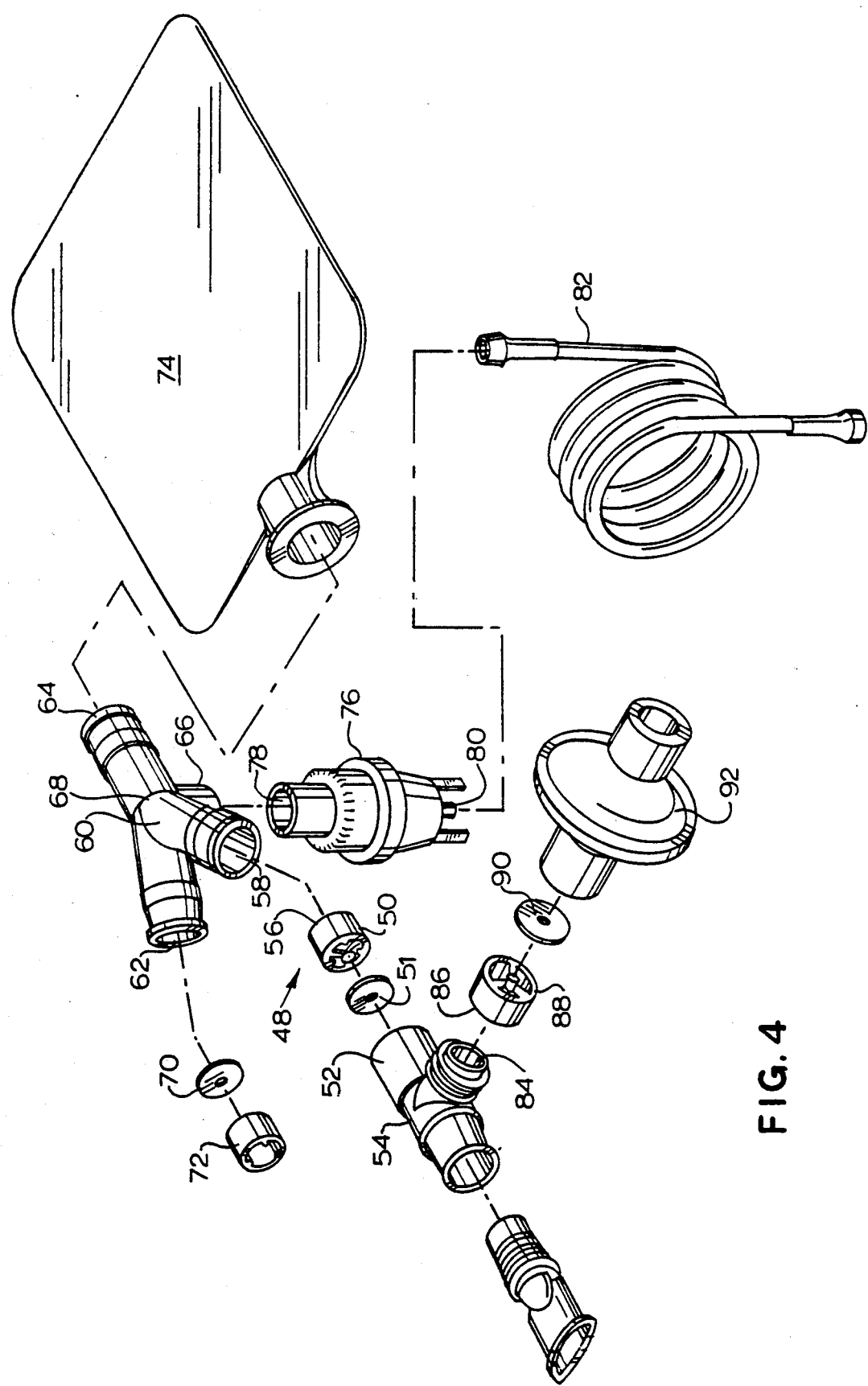
FIG. 4 is an exploded view of the embodiment of the invention illustrated in FIG. 2.

Refer now to FIG. 2, which is another embodiment of the invention. In this figure, the components of the system 10 are located differently, but each component performs the same function of the components illustrated in the embodiment shown in FIGS. 1 and 3. The inlet leg 48 is illustrated in greater detail in FIG. 4. As can be seen in FIG. 4, the inlet leg includes a one-way valve 50 having its outlet side 51 which is connected to one leg 52 of a common juncture 54. The inlet side 56 of valve 50 is connected to one leg 58 of a four-leg manifold 60. Three legs 58, 62 and 64, of the manifold 60 are in the form of a Y connector. A fourth leg 66 extends from the common juncture 68 of the other three legs of the manifold 60. One of the legs 62 of the manifold 60 is connected to the outlet side 70 of a one-way valve 72. The one-way valve 72 allows make-up room air to enter the inlet leg 48 as discussed above.

Another leg 64 of manifold 60 is connected to a flexible reservoir 74. Finally, leg 66 of the manifold 60 is connected to a nebulizer 76. The nebulizer includes an outlet port 78 which is connected to leg 66 of manifold 60 and an inlet port 80 which is connected to a means for providing pressurized air 82 to the nebulizer 76.

Another leg 84 of common juncture 54 is connected to the inlet side 86 of one-way valve 88. The outlet side 90 of one-way valve 88 is connected to a filter 92. The purpose of the filter 92 is identical to the purpose of filter 36 in FIG. 3.

Referring once again to FIG. 2, it can now be understood based on the proceeding discussion of the components in FIG. 4 that the device illustrated in FIG. 2 includes an inlet 48, an outlet leg 94 and a patient breathing leg 96.

Various materials can be used to form the reservoir 74. For example, flexible polyvinyl chloride, low density polyethylene and ethyl vinyl acetate may be used to form the reservoir. In the preferred embodiment, the threshold filling pressure for the reservoir is approximately 0.1 centimeters of water pressure.

I claim:

1. A medication aerosol delivery system for delivering a small particle aerosol to a patient, comprising:
    a manifold including an inlet leg, an outlet leg, and a patient breathing leg, each of said legs being in communication with one another at a common juncture location;
    said inlet leg further including each of the following in communication with one another
        a medication nebulizer for introducing a medicated aerosol into said inlet leg,
        a flexible reservoir to receive medicated aerosol from said nebulizer between patient inhalations,
        a first one-way valve located between said common juncture location and both of said nebulizer and said flexible reservoir to allow air to flow in one direction only from said inlet leg to said patient breathing leg and said outlet leg,
    said first valve having a threshold opening pressure, said flexible reservoir having a threshold filling pressure and a threshold collapsing pressure, said threshold filling pressure of said flexible reservoir being less than said threshold opening pressure of said first one-way valve.

2. A system as recited in claim 1 wherein said flexible reservoir is located between said first valve and said nebulizer.

3. A system as recited in claim 1 wherein said first leg further includes a second one-way valve for introducing make-up room air into said first leg, said second valve having a threshold opening pressure that is greater than said threshold collapsing pressure of said reservoir, said second one-way valve opening to allow make-up room air in said inlet leg only when pressure within said inlet leg becomes less than room pressure by an amount greater than said threshold opening pressure of said second one-way valve.

4. A system as recited in claim 1 wherein said first one-way valve includes a variable orifice which increases with increased differential pressure across said first one-way valve, said variable orifice having a pressure flow characteristic such that a majority of medicated aerosol from said nebulizer flows into said reservoir and a minority of said medicated aerosol flows though said first one-way valve when a patient is not inhaling through said patient breathing leg.

5. A filtered medication aerosol delivery system for delivering a small particle aerosol to a patient comprising:
    a manifold inlet leg, including:
        a room air one-way check valve,
        a first T-connector, said first T-connector having first, second, and third legs, said first T-connector having said first leg connected to said room air one-way check valve,
        a flexible reservoir, said flexible reservoir in fluid communication with said second leg of said first T connector,
        a second T-connector having first, second and third legs, said first leg of said second T-connector being in fluid communication with said third leg of said first T-connector,
        a nebulizer, said nebulizer having an inlet port and an outlet port, said outlet port of said nebulizer being in fluid communication with said second leg of said second T-connector,
        means for supplying a pressurized gas to said inlet port of said nebulizer,
        an inlet leg one-way valve in fluid communication with said third leg of said second T-connector, said one-way valve allowing fluid to flow only from said third leg of said second T-connector through said valve,
    a patient breathing leg including:
        a mouthpiece through which a patient may inhale and exhale,
    an outlet leg including:
        a filter, said filter having an outlet port and an inlet port, an exhalation one-way valve, said exhalation valve being in fluid communication with said inlet port of said filter, and
        a common juncture including a manifold having first, second and third legs, said first leg of said manifold being in fluid communication with said inlet leg one-way valve, said second leg of said manifold being in fluid communication with said mouthpiece, and said third leg of said manifold being in fluid communication with said exhalation one-way valve.

* * * * *